(12) United States Patent
Linz et al.

(10) Patent No.: US 7,033,614 B2
(45) Date of Patent: Apr. 25, 2006

(54) BISMUTH OXYCHLORIDE COMPOSITIONS AND METHODS OF RINSING

(75) Inventors: Phil Linz, Croton-Hudson, NY (US); Rantan K. Chaudhuri, Lincoln Park, NJ (US)

(73) Assignee: EMD Chemicals, Inc. (Previously EM Industries), Hawthorne, NY (US)

( * ) Notice: Subject to any disclaimer, the term of this patent is extended or adjusted under 35 U.S.C. 154(b) by 341 days.

(21) Appl. No.: 10/648,828

(22) Filed: Aug. 27, 2003

(65) Prior Publication Data

US 2005/0048014 A1 Mar. 3, 2005

(51) Int. Cl.
*A61K 7/021* (2006.01)
*A61K 7/08* (2006.01)
*A61K 7/48* (2006.01)
*A61K 7/50* (2006.01)
*A61K 33/00* (2006.01)

(52) U.S. Cl. .................. 424/653; 424/401; 424/70.12; 424/70.19; 424/70.21; 424/70.22; 510/119; 510/122; 510/129; 510/130; 510/136; 510/137; 510/157; 510/158; 510/159; 510/160; 510/419; 510/466; 514/827; 514/828; 514/844; 514/846; 514/848; 514/937; 514/951

(58) Field of Classification Search ................ 424/401, 424/70.12, 70.19, 70.21, 70.22, 653; 510/119, 510/122, 129, 130, 136, 137, 157–160, 419, 510/466; 514/827, 828, 844, 846, 848, 937, 514/951
See application file for complete search history.

(56) References Cited

U.S. PATENT DOCUMENTS

| | | | |
|---|---|---|---|
| 5,000,937 A * | 3/1991 | Grollier et al. ................ 424/47 |
| 6,579,357 B1 * | 6/2003 | Cao ........................... 106/459 |
| 6,743,285 B1 * | 6/2004 | Anselmann et al. ........ 106/415 |
| 6,906,015 B1 * | 6/2005 | Shiloach et al. ............ 510/130 |
| 2004/0076699 A1 * | 4/2004 | Chaudhuri et al. ......... 424/775 |

OTHER PUBLICATIONS

Mitsui, T. New Cosmetic Science, Elsevier, New York, 1999, pp. 410-412.*

* cited by examiner

*Primary Examiner*—John Pak
(74) *Attorney, Agent, or Firm*—Millen, White, Zelano & Branigan, P.C.

(57) ABSTRACT

A rinse-off composition comprising in percent by weight 0.10–10.00 of a dispersion of bismuth oxychloride 3.50–90.00 of a surfactant, 0.001–0.050 of a dye, 3.00–15.00 of an emollient and 10.00–80.00 of water; said dispersion of bismuth oxychloride containing bismuth oxychloride platelet particles having a lateral width of 5–25 microns and a thickness of 20–200 nm, said platelet particles being substantially covered a liquid vehicle and said liquid vehicle being present in an amount sufficient to maintain a stable dispersion and to provide for facile resuspension.

17 Claims, No Drawings

BISMUTH OXYCHLORIDE COMPOSITIONS AND METHODS OF RINSING

CROSS REFERENCE TO RELATED APPLICATIONS

This application relates to U.S. application Ser. No. 10/616,494 filed Jul. 10, 2003, "TOPICAL ANHYDROUS DELIVERY SYSTEM".

SPECIFICATION

The present invention is directed primarily to the field of cosmetics, and in particular to compositions containing bismuth oxychloride, especially rinse-off compositions.

In the cosmetics industry, research is conducted in order to provide improved products which generate a pleasing effect. For example, in so-called rinse-off products, it is desirable to provide skin with a lustrous appearance and a silky feel.

Accordingly, one aspect of this invention is to provide improved cosmetic products and a method of utilizing products so as to obtain a desirable luster and silky feel.

To achieve one aspect of the present invention, there is provided a rinse-off composition comprising a dispersion of bismuth oxychloride (BiOCl) in a liquid vehicle (hereinafter referred to interchangeably as "solvent").

Another aspect of the invention concerns a preferred composition containing a special type of bismuth oxychloride in special types of solvents.

A preferred embodiment of the rinse-off composition comprises a bismuth oxychloride dispersion. This dispersion comprises a lustrous bismuth oxychloride dispersed in an octyl-hydroxy stearate solvent., e.g. the commercial product BIRON® LIQUID SILVER from EMD Chemicals, Inc. In general the amount of solvent is enough to maintain a stable dispersion and to provide for facile resuspension, e.g. 10–80%, by weight, especially 20–40% by weight, and preferably about 30% by weight. The remaining bismuth oxychloride e.g. 20–90% by weight, especially, 60–80% by weight, preferably about 70% by weight generally comprises platelet particles with a lateral breadth (diameter) of 5–25 microns, preferably 10–15 microns and a thickness of 20–200 nm, preferably 40–80 nm, with smooth surfaces, and are dispersed nearly parallel to each other over the entire area.

In the preferred Biron® Liquid Silver dispersion, the lateral surface is substantially covered by a liquid phase, e.g. at least about 90% of the pigment area, in order to achieve the desired lustrous appearance.

The method of forming the dispersion comprises two main process steps: (A) formation of the platelet shaped BiOCl crystals by precipitation in an aqueous medium and (B) transfer of the suspension into a liquid vehicle. More specifically, platelet shaped BiOCl particles are formed by hydrolyzing a solution of a bismuth salt (e.g. bismuth nitrate) which is formed by dissolving the salt in an aqueous mineral acid (e.g. nitric or hydrochloric). The bismuth salt solution is slowly fed into a reactor containing water, which is typically acidified, preferably in a pH range 0.5 to 2.0, and which also contains chloride in the form of hydrochloric acid or alkali (ammonium, sodium or potassium) chloride salt. (Note that chloride in the reactor is required only if insufficient hydrochloric acid to provide enough chloride at a mol ratio to the bismuth of 1:1 is not employed in the bismuth salt solution). Alternatively, a solution of alkali hydroxide can be fed concurrently with the bismuth salt solution into reactor to maintain the pH in the initial pH range. Directly, a suspension of platelet-shaped BiOCl crystals is formed in the acidified salt solution (a.k.a. mother liquor). The acids and salts in the mother liquor are removed from the suspension by elutriation (sedimentation followed by decanting and backfilling with deionized water). (Sedimentation can be achieved by centrifugation using decanter devices).

The BiOCl sediment in the acid-and salt-free sediment is admixed with a volatile solvent or alternatively the liquid vehicle itself. Such liquids are chosen which preferentially wet the surface of the BiOCl particles and displace the water. As much water as possible is removed by decanting after several more portions of volatile solvent are admixed. In order for the liquid vehicle to be retained in the final dispersion, it must be substantially less volatile than water, than the solvent or than the azeotropic mixture of the water and solvent and/or liquid vehicle. It is preferable that the liquid vehicle be non-volatile or nearly non-volatile.) The liquid vehicle is then admixed if not admixed previously. While mixing, for example, with a set of anchor-type impeller blades in a kettle reactor, heat and vacuum are applied to accelerate the evaporation of residual water and solvent, leaving behind BiOCl and liquid vehicle. Additional liquid vehicle or other components can be admixed as necessary to achieve the desired composition.

Aside from octyl-hydroxy stearates (Syn. ethyl hexyl hydroxy stearate), there can be employed equivalent solvents having the characteristics of the latter solvent such characteristics being, for example, viscosity, emolliency, suspension ability, low (bland) odor potential, low oxidation potential, pale color, clarity. In addition, the liquid vehicle should be relatively non-volatile, i.e. slower evaporating than water and most solvents, preferably with a boiling point much greater than 150° C. and negligible vapor pressure up to 100° C. It is also preferably lipophilic rather than hydrophilic, and preferably should be a liquid at room temperature i.e. have a melting point below 20° C.

Whereas, it would be impossible to list all known equivalent liquid vehicles as well as those known in the future, examples of known equivalent solvents include but not limited to mineral oils, vegetable oils including but not limited to sweet almond oil, wheat germ oil, jojoba oil, apricot kernel oil, soybean oil, canola oil, kiwi fruit seed oil, kukui nut oil; modified vegetable oils such as maleated soybean oil; esters such as propylene glycol dicaprylate/dicaprate, octyl dodecanol, octyldodecyl neopenanoate, cocglycerides, caprylic/capric triglycerides, tri-octyldodecyl citrate, pentaerythrityl tetraiosostearate, isodecyl neopentanoate, diisopropyl sebacate, C12–15 alkyl benzoate, ethylhexyl ethylhexanoate; or silicone fluids such as cyclomethicone, (by itself and in combination with dimethicone crosspolymer), isostearyl trimethylopropane siloxy silicate, dimethicone, cyclopentasiloxane, and polysilicones. Mixtures of such solvents are also contemplated.

In conjunction with the solvents which are employed in dispersion-providing concentrations, it is to be understood that other bismuth oxychloride pigments can be utilized, but with less desirable results for example agglomerated powdered bismuth oxychloride pigments, e.g., Biron® B-50, Biron® ESQ, Biron® Fines, Biron® MTU or Biron® LF-2000.

The preferred rinse-off cleansing product of the present invention, by virtue of the presence of Biron® Liquid Silver, has a unique pale, highly-lustrous silverwhite pearlescent In general the final rinse-off product comprises other ingredients as follows:

| COMPONENT | % BY WEIGHT General | Preferred |
|---|---|---|
| Biron ® Liquid Silver or Equivalent | 0.10–10.00 | 0.50–2.00 |
| Surfactant | 30.50–90.00 | 40.00–65.00 |
| Dye | 0.001–0.050 | 0.005–0.020 |
| Emollient | 3.00–15.00 | 2.00–8.00 |
| Water | 10.00–80.00 | 15.00–40.0 |

The surfactants can be any of anionic, nonionic or amphoteric surfactants. The dyes are generally "FD&C" dyes. The emollient can be any conventional compound, examples including but not limited to silicones, cosmetically-acceptable esters or oils such as ethyhexyl hydroxystearate, mineral and vegetable oils, and the other compounds noted above as equivalent liquid vehicles. In addition, optional conventional thickeners, preservatives, moisturizers, plant extracts, vitamins, anti-oxidants, etc. can be included.

The personal rinse-off cleansing compositions of the present invention, having a bright pearlescence-shade appearance, provide excellent rinse, feel, skin mildness and foaming. The metal-like sharp and brilliant luster achieved with the BiOCl dispersion cannot be mimicked by utilizing mica, either in a fine or large particle size or a bismuth oxychloride powder, due to the facts that high-luster bismuth oxychloride is innately more lustrous than mica, and that bismuth oxychloride powders show high degrees of agglomeration, which causes the luster in such a product to be greatly diminished.

In addition to personal cleansing compositions, the bismuth oxychloride dispersions can be used in hair shampoo or conditioner formulations or syndet bars but in such cases there would be modifications of the rinse-off formulations, for example, in the case of shampoos, the final product must be an emulsion or a microemulsion, in order to incorporate the bismuth dispersion in the oil phase. In the case of the syndet bars, care must be taken to ensure that the bismuth dispersion (oil phase) is completely and uniformly dispersed throughout the matrix.

The amount of rinse-off product applied to skin varies, for example: typical use directions would include instructions to the user to "squeeze a small amount of product onto wet puff. Lather and rinse." A typical amount put onto the puff would generally be about 3–5 grams of product. The product could then be re-applied, as needed.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above or below is hereby incorporated by reference.

Attachment-1

EXAMPLE-1

Moisturizing Body Wash with BIRON® Liquid Silver (PL-6-53D)

| INCI NAME | TRADE NAME/ MANUFACTURER | % |
|---|---|---|
| Phase A | | |
| Deionized Water | Water | q.s. to 100.00 |
| Tetrasodium EDTA | Hamp-ene 220/Hampshire Chemical | 0.05 |
| Acrylates Copolymer | Carbopol Aqua SF-1/ Noveon | 5.00 |
| Glycerine | Emery 916/Cognis | 3.50 |
| Phase B | | |
| Ammonium Lauryl Sulfate | Standapol A/Cognis | 19.45 |
| Sodium Laureth Sulfate | Standapol ES-2/Cognis | 15.00 |
| Coco-Betaine | Velvetex AB-45/Cognis | 20.00 |
| Phase C | | |
| Sodium Cocoamphoacetate | Monateric CM-36/ Uniquema | 5.00 |
| Phase D | | |
| Ethylhexyl Hydroxystearate | Schercemol OHS/Scher | 2.50 |
| Cyclomethicone | Dow Corning 345 Fluid/ Dow Corning | 1.20 |
| Cyclomethicone (and) Dimethicone Crosspolymer | Dow Corning 9040 Silicone Elastomer Blend/Dow Corning | 1.80 |
| PEG-8 Beeswax | Apfil Pastilles/Gattefosse | 2.50 |
| Glyceryl Dibehenate (and) Tribehenin (and) Glyceryl Behenate | Compritol 888 ATO/ Gattefosse | 2.50 |
| Bismuth Oxychloride (and) Ethylhexyl Hydroxystearate | Biron ® Liquid Silver/ Rona | 1.00 |
| Phase E | | |
| Propylene Glycol (and) Diazolidinyl Urea (and) Methylparaben (and) Propylparaben | Germaben II/Sutton | 1.00 |
| Fragrance | Grapefruit Fragrance 26520M/Shaw Mudge | 0.20 |
| Total | | 100.00 |

Procedure: Blend ingredients in Phase A with mixing; the mixture should be smooth and homogeneous before proceeding. Add ingredients in Phase B with mixing and heating. Once the blend is homogenous, add Phase C with mixing. Heat to 70°–75° C. Combine ingredients in Phase D and heat to 70°–75° C. Add Phase D to Phases ABC; continue mixing. Homogenize. Adjust pH (if necessary to 5.5–7.0). At 40° add Phase E and mix until uniform.

Salient features of this composition:

| Ingredient | Function |
|---|---|
| Water | Matrix |
| Carbopol | Thickener, suspension agent |
| Glycerine | Humectant; increased skin feel |

-continued

| Ingredient | Function |
|---|---|
| Ammonium Lauryl Sulftate | Primary surfactant (anionic) |
| Sodium Laureth Sulftate | Primary Surfactant (anionic) |
| Coco-Betaine | Surfactant; foam-booster (zwitterionic salt) |
| Sodium Cocozmphoacetate | Surfactant (ampohteric); pH adjuster |
| Ethylhexyl Hydroxystearate | Emollient |
| Cyclomethicone, Silicone Gel | Skin feel |
| Apfil + Compritol | Emulsifiers |
| Biron Liquid Silver | Bright, clean, silvery pearlescent pigment. |

EXAMPLES A–K

These examples, two sets of compositions with different dyes, were prepared by utilizing the body wash composition of Example 1, and different forms of bismuth oxychloride, as follows:

The pigment type was varied between:
a) High-luster BiOCl in dispersion (ethylhexyl hydroxysterate): Biron® Liquid Silver;
b) High-luster BiOCl in dispersion (castor oil)" Biron® Silver CO:
c) Powdered BiOCl: Biron® LF-2000
d) Large-particle sized [10–150 (80% within range) 65–82 μm (D50, median size)] mica pigment: Timiron® MP-149; and
e) Small-particle sized [<15 μm, (80% within range), 3–10 μm (D50, median size)] mica pigment: Timiron® MP-1005.

In the following tests, blue dye was added to the first set (0.11% of a 2% Blue 1 solution in water) and blue and yellow dye (0.11% of a 2% Blue 1 solution plus 0.39% of 2% yellow 5 solution in water) were added to the second set, giving one set with a blue mass color and one with a green mass color.

The results of such tests are tabulated as follows:

Both systems illustrate that the addition of high-luster BiOCl dispersions will increase pearlescence and whiten the system better than powdered BiOCl or mica-based pearlescent pigments.

Also, Biron® Liquid Silver (high-luster BiOCl dispersion in ethylhexyl hydroxysterate) performed significantly better than Biron® Silver CO (high-luster BiOCl dispersion in castor oil).

Body washes can be prepared as illustrated by Rona Formula No. PL-6-53D. The system described in that formula represents a body wash which uses a dispersion of high-luster bismuth oxychloride in cosmetic-grade ester ethylhexyl hydroxysterate to create a product with a very highly-lustrous, pearlescent appearance. The degree of pearlescence shown in this product is greater than an be obtained with conventional mica-based pearlescent pigments, powdered bismuth oxychloride pigments, or commercially-available high-luster bismuth oxychloride dispersions in such vehicles are castor oil or mineral oil.

The specific of compositions of the product containing Biron® Liquid Silver preferably comprise the following components:

Water, as a diluent.

EDTA, as a chelating agent.

A thickening and/or suspending agent, such as xanthan gum, magnesium aluminum silicate, hectorite, cellulose gums, carbopol or other acrylate polymer systems such as Simulgel EG (Seppic). Structure Plus (National Starch) or Synthalen W2000 (3V), either alone or in combination.

A humectant, such as glycerine or propylene glycol.

Anionic surfactants, chosen from the list of sodium, potassium or ammonium lauryl sulfates, sodium, potassium or ammonium laureth sulfates, betaines, sulfosuccinates, alkyl polyglycosides, cocoyl sarcosinates, cocoyl isethionates, etc.

|  | Control; No Pigment Added | Biron® Liquid Silver | Timiron® MP-149 | Timiron® MP-1005 | Biron® LF-2000 | Birion® Silver CO |
|---|---|---|---|---|---|---|
| Formula No. | PL-6-53E | PL-6-53F | PL-6-53G | PL-6-53H | PL-6-53J | PL-6-53K |
| Color | Blue | Very Pale Blue | Blue | Light Blue | Blue | Pale Blue |
| Pearlescence | None | High; Satiny | Low-Moderate; Sparkly | Moderate; satiny | Very Slight | Moderate-High; Satiny |
| Pearlescence Rank* | 6 | 1 | 4 | 3 | 5 | 2 |
| Formula No. | PL-6-56A | PL-6-56B | PL-6-56D | PL-6-56E | PL-6-56F | PL-6-56C |
| Color | Green | Very Pale Green | Green | Light Green | Green | Pale Green |
| Pearlescence | None | High; Satiny | Low-Moderate; Sparkly | Moderate; Satiny | Very slight | Moderate-High; Satiny |
| Pearlescence Rank* | 6 | 1 | 4 | 3 | 5 | 2 |

*Pearlescence rank indicates rating of pearlescent appearance in these systems, with 1 representing the highest pearlescence shown and 6 being the least.

An amphoteric surfactant, such as sodium cocoamphoacetate.

An oil phase comprising of emollients such as ethylhexyl hydroxysterate, cocoglycerides, caprylic/capric triglycerides, propylene glycol dicaprylate/dicaprate, myristyl myristate, mineral oil, sweet almond oil, wheat germ oil, and jojoba oil; silicone fluids such as cyclomethicone, dimethicone, dimethiconol, and dimethicone crosspolymer, and and emulsifier system, such as the combination of PEG-8 beeswax, glyceryl dibehenate, tribehenin, and glyceryl behenate.

High-luster bismuth oxychloride in ethylhexyl hydroxysteate.

A preservative system and fragrance.

The following table describes preferred products, incorporating Biron® Liquid Silver in parts by weight:

| Ingredient | Broad Range (%) | Preferred Range (%) |
|---|---|---|
| Water | 10.00–80.00 | 15.00–40.00 |
| Na$_2$ EDTA | 0.01–0.10 | 0.02–0.07 |
| Carbopol (liquid; 15% active in water) | 2.00–10.00 | 4.00–8.00 |
| Humectant | 0.50–10.00 | 2.00–8.00 |
| Anionic Surfactants | 30.00–80.00 | 40.00–65.00 |
| Amphoteric Surfactant | 0.50–10.00 | 2.00–8.00 |
| Emollients (including silicone fluids) | 3.00–15.00 | 2.00–8.00 |
| Emulsifier system | 2.00–10.00 | 3.00–6.00 |
| Bismuth oxychloride dispersion, Biron ® Liquid Silver) | 0.10–10.00 | 0.50–1.50 |
| Preservative | 0.20–2.00 | 0.50–1.50 |
| Fragrance | 0.05–0.50 | 0.10–0.30 |

EXAMPLE 2

Mild Syndet Soap Bar with BIRON® Liquid Silver (PL-6-65A)

| INCI NAME | TRADE NAME/MANUFACTURER | % |
|---|---|---|
| Phase A | | |
| Lauroyl Sarcosine | Hamposyl L/Hampshire Chemical | 30.00 |
| Bismuth Oxychloride (and) Ethylhexyl Hydroxystearate | Biron ® Liquid Silver/Rona | 1.00 |
| Stearic Acid | Emersol 132/Cognis | 31.00 |
| Sodium Cocoyl Isethionate | Tauranol I-78/Finetex | 30.00 |
| Phase B | | |
| Sodium Hydroxide | Unichem SOHYD/Universal Preserv-A-Chem | 4.00 |
| Water | Water, Demineralized | 4.00 |
| Total | | 100.00 |

Procedure: Heat lauryol sarcosine to 55° C. Add Biron® Liquid Silver with mixing. Add stearic acid and mix until dissolved. Add sodium cocoyl isethionate with mixing and allow to dissolve. Blend ingredients in Phase B. Neutralize Phase A with gradual additions of 50% NaOH solution. Check pH during neutralization by adding aliquots of the molten mixture to deionized water. Neutralize to pH 5.5–6.5. Add fragrance or other ingredients if desired. Pour warm homogeneous mixture into molds and allow to set at room temperature.

EXAMPLE 3

Pearlescent Shampoo with BIRON® Liquid Silver (PL-6-66A)

| INCI NAME | TRADE NAME/MANUFACTURER | % |
|---|---|---|
| Phase A | | |
| Magnesium Aluminum Silicate | Veegum HV/Vanderbilt | 0.700 |
| Hydroxypropylcellulose | Klucel G/Aqualon | 1.000 |
| Water | Demineralized Water | 39.300 |
| Phase B | | |
| Citric Acid | Citric Acid/EMD Chemicals | 0.100 |
| Sodium Chloride | Sodium Chloride/Cargill | 2.000 |
| Water | Demineralized Water | 12.000 |
| Phase C | | |
| TEA Lauryl Sulfate | Standapol T/Cognis | 12.300 |
| Water | Demineralized Water | 12.000 |
| Phase D | | |
| Cocamidopropyl Betaine | Velvetex BA-35/Cognis | 5.000 |
| Cocamide DEA | Standamid KD/Cognis | 3.000 |
| Bismuth Oxychloride (and) Ethylhexyl Hydroxystearate | Biron ® Liquid Silver/Rona | 0.50 |
| Methylparaben | Methylparaben/Spectrum Chemical | 0.200 |
| Diazolidinyl Urea | Germall II/Sutton | 0.300 |
| Phase E | | |
| Blue 1 | FD&C Blue No. 1 10-21-DA-2204/Hilton-Davis | 0.002–0.030 |
| Water | Demineralized Water | q.s. to 100.000 |
| Total | | 100.00 |

Procedure: Disperse the Veegum and Klucel in water with a high-speed mixer until no undispersed particles remain. Dissolve the sodium chloride and citric acid in the water of Phase B and add to the batch. Combine Phase C and add to the batch. Combine Phase D and add to the batch. Disperse the dye in the water of Phase E; mix until no undispersed particles remain, and add to the batch. Comtinue mixing until the batch is smooth and uniform.

EXAMPLE 4

Hair Conditioner with Biron Liquid Silver (PL-6-67 A)

| INCI NAME | TRADE NAME/ MANUFACTURER | % |
|---|---|---|
| Phase A | | |
| Water | Deionized Water | 90.50 |
| Hydroxycellulose | Cellosize PCG-10 | 0.80 |
| Phase B | | |
| Propylene Glycol | Propylene Glycol/Lyondell | 1.50 |
| Methylparaben | Nipagin M/Nipa | 0.20 |
| Phase C | | |
| Cetyl Alcohol | Lanette 16/Henkel | 2.00 |
| Cetearyl Alcohol (and) Ceteareth-20 | Promulgen D/Amerchol | 4.50 |
| Bismuth Oxychloride (and Ethylhexyl Hydroxystearate | Biron Liquid Silver/Rona | 0.50 |
| Total | | 100.00 |

Procedure: Disperse hydroxycellulose in water. Heat to 70°–75° C. and continue mixing until the powder is fully hydrated and the mixture is smooth and homogeneous. Blend ingredients in Phase B and add to Pheuse A. Combine ingredients in Phase C and heat to 70°–75° C. with mixing. Slowly add Phase C to the batch with stirring; mix until uniform. Cool to 25° C. and adjust pH (if necessary) to 4.0–5.5.

The preceding examples can be repeated with similar success by substituting the generically or specifically described reactants and/or operating conditions of this invention for those used in the preceding examples. Examples 2, 3, and 4 on pages 10, 11 and 12.

The entire disclosure of all applications, patents and publications, cited above or below, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions. For example, BIRON® LIQUID SILVER and the like can be incorporated in other compositions such as, for example, lipsticks, eye shadows, pressed powders, rouges, hot-pour cosmetics, mascaras, gels, glosses, base make-up, lotions, balms, creams, ointments, shampoos, perfumes, body washes, soaps, antiperspirants and deodorants, etc.

The invention claimed is:

1. A rinse-off composition comprising in percent by weight 0.10–10.00 of a dispersion of bismuth oxychloride, 3.50–90.00 of a surfactant, 0.001–0.050 of a dye, 3.00–15.00 of an emollient and 10.00–80.00 of water; said dispersion of bismuth oxchioride comprising bismuth oxychloride platelet particles having a lateral width of 5–25 microns and a thickness of 20–200 nm, said platelet particles being substantially covered by a liquid vehicle and said liquid vehicle being present in an amount sufficient to maintain a stable dispersion and to provide for a facile resuspension.

2. A rinse-off composition according to claim 1, wherein said liquid vehicle is present in the dispersion in a concentration of about 10–80% by weight.

3. A rinse-off composition according to claim 1, wherein the liquid vehicle is present in the dispersion in a concentration of about 20–40% by weight.

4. A rinse-off composition according to claim 3, wherein the lateral width of the bismuth oxychloride platelet particles is 10–15 microns and the thickness of said platelet particles is 40–80 nm.

5. A rinse-off composition according to claim 4, wherein the bismuth oxychloride is present in the dispersion in a concentration of about 70% by weight and the liquid vehicle is present in the dispersion in a concentration of about 30% by weight.

6. A rinse-off composition according to claim 1, wherein the liquid vehicle comprises octyl-hydroxy stearate.

7. A rinse-off composition according to claim 1, comprising in percent by weight 0.50–2.00 of a dispersion of bismuth oxychloride, 40.00–65.00 surfactant, 0.005–0.20 of dye, 2.00–8.00 of emollient, and 15.00–40.00 of water.

8. A rinse-off composition according to claim 1, wherein said liquid vehicle has properties of viscosity, emolliency, suspension ability, low oxidation potential, pale color and clarity equivalent to octyl-hydroxy stearate, and is slower evaporating than water, has a boiling point greater than 150° C., is lipophilic, and is liquid at room temperature.

9. A rinse-off composition according to claim 7, wherein said liquid vehicle has properties of viscosity, emollency, suspension ability, low oxidation potential, pale color and clarity equivalent to octyl-hydroxy stearate, and is slower evaporating than water, has a boiling point greater than 150° C., is lipophilic and is liquid at room temperature.

10. A rinse-off composition according to claim 2, wherein the liquid vehicle comprises octyl-hydroxy stearate.

11. A rinse-off composition according to claim 3, wherein the liquid vehicle comprises octyl-hydroxy stearate.

12. A rinse-off composition according to claim 4, wherein the liquid vehicle comprises octyl-hydroxy stearate.

13. A rinse-off composition according to claim 1, wherein said surfactant comprises a combination of anionic surfactant and amphoteric surfactant and said emollient comprises silicone fluids.

14. A rinse-off composition according to claim 4, wherein said surfactant comprises a combination of anionic surfactant and amphoteric surfactant and said emollient comprises silicone fluids.

15. A rinse-off composition according to claim 6, wherein said surfactant comprises a combination of anionic surfactant and amphoteric surfactant and said emollient comprises silicone fluids.

16. A rinse-off composition according to claim 7, wherein the liquid vehicle consists essentially of octyl hydroxystearate.

17. A rinse-off composition according to claim 15, and wherein the liquid vehicle consists essentially of octyl hydroxysterate.

* * * * *